United States Patent
Cheong et al.

(10) Patent No.: US 10,406,378 B2
(45) Date of Patent: Sep. 10, 2019

(54) ALTERNATIVE MAGNETIC STIMULATING SYSTEM FOR PREVENTING OR TREATING BRAIN TUMOR GROWTH

(71) Applicant: Industry-Academic Cooperation Foundation, Yonsei University, Seoul (KR)

(72) Inventors: Eun Ji Cheong, Seoul (KR); Do Guwn Hwang, Gangwon-Do (KR); Go Eun Ha, Seoul (KR); Yi An Chen, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 377 days.

(21) Appl. No.: 14/935,779

(22) Filed: Nov. 9, 2015

(65) Prior Publication Data
US 2016/0228722 A1    Aug. 11, 2016

(30) Foreign Application Priority Data

Feb. 9, 2015    (KR) .......................... 10-2015-0019431

(51) Int. Cl.
*A61N 2/02*    (2006.01)
*A61N 2/00*    (2006.01)

(52) U.S. Cl.
CPC ............... *A61N 2/02* (2013.01); *A61N 2/004* (2013.01)

(58) Field of Classification Search
CPC .......... A61N 2/00; A61N 2/002; A61N 2/004; A61N 2/006; A61N 2/008; A61N 2/02; A61N 2/06; A61N 2/12; A61N 1/40
See application file for complete search history.

(56) References Cited

U.S. PATENT DOCUMENTS 5,156,587 A * 10/1992 Montone .................. A61N 2/02
                                                                600/13
6,210,317 B1 * 4/2001 Bonlie ...................... A61N 2/02
                                                                 600/9

(Continued)

FOREIGN PATENT DOCUMENTS

| JP | 2005-350396 A | 12/2005 |
| KR | 10-2010-0031654 A | 3/2010 |
| KR | 10-2014-0056853 A | 5/2014 |

OTHER PUBLICATIONS

Chen, Yi-An, "Alternating Magnetic Stimulation Suppresses the Proliferation and Migration of Glioblastoma Cells", Brain Conference 2014, Joint Conference of the KSBNS, CASN, and KSND, Nov. 6-8, 2014, English Abstract, 2 pages.

*Primary Examiner* — Carrie R Dorna
(74) *Attorney, Agent, or Firm* — Mintz Levin Cohn Ferris Glovsky and Popeo, P.C.; Kongsik Kim; Derek E. Constantine (57) ABSTRACT

Disclosed herein is a bidirectional alternating application system for preventing or treating a brain tumor caused by malignant glioma cells in animals. The bidirectional alternating magnetic field application system can apply a magnetic field having weak intensity and low frequency to patients in need of the prevention or treatment of brain tumor to thereby specifically inhibit the proliferation and mobility of glioma cells without causing any damage to normal cells. Thus, the bidirectional alternating magnetic field application system can greatly reduce side effects occurring in patients after surgery.

3 Claims, 5 Drawing Sheets (56) References Cited

U.S. PATENT DOCUMENTS

| | | | | |
|---|---|---|---|---|
| 8,376,925 B1* | 2/2013 | Dennis | ................... | A61N 2/004 600/14 |
| 2005/0182288 A1* | 8/2005 | Zabara | ............... | A61N 1/36025 600/14 |
| 2008/0200749 A1* | 8/2008 | Zheng | ................... | A61N 2/006 600/13 |

* cited by examiner

ALTERNATIVE MAGNETIC STIMULATING SYSTEM FOR PREVENTING OR TREATING BRAIN TUMOR GROWTH

CROSS REFERENCE TO RELATED APPLICATION

This application claims priority to Korean Application No. 10-2015-0019431 filed on Feb. 9, 2015, which is incorporated herein by reference.

BACKGROUND OF THE INVENTION

Field of the Invention

The present invention relates to a bidirectional alternating magnetic field application system for preventing or treating brain tumor and to a method for applying magnetic field using the same. Moreover, the present invention relates to a method for treating or preventing brain tumor, in which a bidirectional alternating magnetic field application system that generates a weak magnetic field is used to specifically inhibit the proliferation of malignant brain glioma cells and reduce the mobility thereof without causing damage to normal cells.

Description of the Prior Art

Malignant brain glioma is a kind of cancer disease that occurs when glial cells in the brain develop into cancer cells. More than half of gliomas are malignant, and even benign gliomas show a tendency to develop into malignancy with the passage of time. About 60% of cancers that develop in the brain are malignant gliomas, and the incidence thereof not only in the USA and Europe but also in Korea is increasing. Malignant glioma rapidly metastasizes as cancer cells rapidly penetrate the surrounding tissues. Unlike other cancers, malignant glioma is a disease requiring immediate medical remedy, since glial cells, which develop into malignancy rapidly even without differentiation between phases 1 and 2, penetrate the surrounding brain tissues, causing palsy, convulsion, headache or, disorders of consciousness.

Malignant glioma can be diagnosed by computed tomography (CT), magnetic resonance imaging (MRI), positron emission tomography (PET) or the like, which is used to measure tumor characteristics (e.g., location, area and malignancy).

General methods for brain tumor treatment, which are currently performed in clinical hospitals, include tumor removal surgery, radiotherapy and anticancer chemotherapy. Tumor removal surgery is a method for removing tissues developed into malignant glioma. It can minimize the volume of tumor, and thus can substantially reduce problems such as an increase in brain pressure, which occurs in some tumors. However, malignant glioma tissue has characteristics in that its boundary with normal tissue is unclear and it grows at a very high rate. Due to such characteristics, in many cases, it is impossible to completely remove the malignant glioma tissue by surgery. For this reason, for most malignant glioma patients, it is required to take continuous radiotherapy and anticancer chemotherapy therapy in combination even after surgery. Radiotherapy is a therapeutic method that is applied to exterminate tumor cells capable of remaining after tumor removal surgery and to delay the growth of the tumor cells. In radiotherapy, a total of about 60 Gy of radiation dose is irradiated in divided doses over 6-7 weeks. However, radiotherapy also affects normal proliferating cells, resulting in side effects such as salivary gland damage or hair loss. Anticancer chemotherapy is a therapeutic method that is applied to exterminate tumor cells remaining after tumor removal surgery and to delay the growth of the tumor cells. Standard anticancer chemotherapy is carried out with Temozolomide approved by the FDA, but causes side effects such as vomiting, giddiness, headache, a decrease of appetite, physical degradation, or temporary hair loss. In the case of elderly patients, tumor tissue removal surgery is not performed in order to reduce burden on the body, but it is general to perform radiotherapy and chemotherapy in combination. However, even when this combination therapy is applied to brain tumor patients, the mean survival time of these brain tumor patients is 12-15 months, and the survival rate of the patients is low even when the patients are treated with surgery and other therapies. In addition, when tumor cells penetrate tissue and are present therein, the possibility of recurrence of the tumor is high. As described above, malignant glioma is a disease having a very high possibility of recurrence even after surgery and difficult to cure completely.

Meanwhile, there were attempts to treat malignant glioma using a magnetic field. Korean Patent Application No. 2009-0078310 discloses a method for inhibiting cancer cell growth using a magnetic field (Patent Document 1). Patent Document 1 is characterized in that a unidirectional magnetic field having a strong intensity (2,000 Gauss (0.2 T)), generated from a direct current system comprising a permanent magnet or an electromagnet is applied. However, in this method, there is a high risk of damage to normal cells due to strong magnetic field intensity. In addition, PCT publication no. WO2013/121359 discloses a method for treating brain disease using a transcranial magnetic stimulation device, particularly a pulse magnetic field (Patent Document 2). Another prior art discloses a method for treating malignant glioma using magnetic nanoparticles (Non-Patent Document 1: Andreas Jordan et al.). Non-Patent Document 1 relates to a thermal therapy employing a high frequency of 100 kHz. However, in these conventional technologies, damage to normal cells is greatly doubtful, because a magnetic field having a very strong intensity in a high frequency range is applied in order to inhibit the proliferation of tumor cells. In addition, these conventional technologies do not propose a solution to the problem of inhibition of the metastasis of glial cells to the surrounding tissue, which is the most important problem in the treatment of malignant glioma.

Accordingly, the present inventors have surprisingly found that, when a bidirectional alternating magnetic field is generated and applied to malignant gioma cells, the proliferation of the malignant glial cells is effectively inhibited in a frequency range significantly lower than those used in the conventional technologies, thereby completing the present invention. In addition, the present invention enables only malignant glioma cells to be specifically inhibited without causing damage to normal cells, and can reduce the mobility of these glioma cells to thereby effectively inhibit the metastasis of brain tumor.

PRIOR ART DOCUMENTS

Patent Documents

Patent Document 1: Korean Patent Laid-Open Publication No. 10-2010-0031654;
Patent Document 2: International Patent Publication No. WO 2013-121359.

Non-Patent Documents

Non-Patent Document 1: Andreas Jordan and Roland Felix, 2006, Journal of Neuro-Oncology 78; 7-14.

SUMMARY OF THE INVENTION

Therefore, it is an object of the present invention to provide a bidirectional alternating magnetic field application system for inhibiting the proliferation of malignant glioma cells.

Another object of the present invention is to provide a bidirectional alternating magnetic field application system for inhibiting the mobility of malignant glioma cells to inhibit the rapid spread of malignant brain tumor.

Still another object of the present invention is to provide a method of preventing or treating brain tumor by applying a bidirectional alternating magnetic field application system to a patient in need of the prevention or treatment of brain tumor.

Still another object of the present invention is to provide a bidirectional alternating magnetic field application system that specifically inhibits the proliferation of malignant glioma cells in the human body without causing damage to normal cells and that reduces the mobility or activity of malignant glioma cells to thereby prevent the metastasis thereof.

To achieve the above objects, the present invention provides a bidirectional alternating magnetic field application system.

In an embodiment, the bidirectional alternating magnetic field application system includes: a coil unit configured to generate an alternating magnetic field; and a magnetic field application unit configured to apply magnetic field stimulation. If necessary, the bidirectional alternating magnetic field application system may further include a cooling unit for maintaining temperature, a display unit, and a control unit. In addition, the structure of the application unit may have various configurations depending on a subject or a patient. The intensity of the magnetic field being applied may be 20-300 Gauss (0.002-0.03 Tesla), preferably 50-200 Gauss (0.005-0.02 Tesla).

In another embodiment, the slope of a change in the instantaneous magnetic field intensity of the magnetic field being applied from the bidirectional alternating magnetic field application system of the present invention may be 50 Gauss/100 microsec or less.

In still another embodiment, the magnetic field being applied from the bidirectional alternating magnetic field application system of the present invention has a frequency ranging from 200 Hz to less than 1000 Hz. Preferably, the frequency of the magnetic field is 300-500 Hz.

In still another embodiment, the present invention provides a method of preventing or treating a brain tumor caused by malignant glioma cells in animals, including mammals, by use of the bidirectional alternating magnetic field application system. For prevention or treatment of the brain tumor, a magnetic field generated from the bidirectional alternating magnetic field application system of the present invention is applied continuously or discontinuously over about 24-72 hours to a subject or patient in need of this prevention or treatment.

In still another embodiment, the present invention provides a method of inhibiting the rapid metastasis of malignant glioma cells by use of the bidirectional alternating magnetic field application system.

As used herein, the term "magnetic field" means a space in which a magnetic force exists and which can be produced around a changing electric field by a magnetic or a current. A magnetic field influences moving charges, and moving charges can generate a magnetic field. A magnetic field is a vector quantity with magnitude and direction, and the magnitude of the magnetic field is expressed as magnetic field H (magnetic intensity) or magnetic field B (magnetic flux density). Magnetic field H is the quantity that does not consider the magnetic characteristic of a space in which a magnetic field acts, and magnetic field B is the quantity that considers the magnetic characteristic of a space, and is used directly to calculate a magnetic force. Magnetic field H and magnetic field B have the following relationship: $B=\mu H$, wherein $\mu$ is magnetic permeability which is the magnetic characteristic of a space in which a magnetic field acts. The magnetic field is directed from the N-pole to the S-pole, which is the direction of a force that is applied to the N-pole of a magnetic compass needle in the magnetic field. The magnetic field can be expressed as magnetic force lines, and when it moves along the direction of the N-pole of the magnetic compass needle in the magnetic field, single curves are drawn. These curves are the magnetic force lines and are closed curves going from the N-pole to the S-pole. The density of the magnetic force lines indicates the intensity of the magnetic field. A shorter spacing between the magnetic force lines indicates a higher magnetic field intensity. The number of magnetic force lines per unit area (magnetic flux) is magnetic field B. The unit of magnetic field B is T (Tesla), and 1 G (Gauss) is $10^{-4}$ T. Magnetic flux is expressed as $\Phi$, and the unit thereof is Wb. Thus, magnetic flux and magnetic force are in the following relationship:

$B=\Phi/S$, 1 $T=1$ $Wb/m^2$

"Oscillation frequency" and "frequency" as used herein are understood to have the same meaning. In addition, in the present invention, the mobility and activity of cells are used to describe the ability of glioma cells to penetrate other tissues, and are understood to have the same meaning.

DETAILED DESCRIPTION OF THE INVENTION

Hereinafter, the present invention will be described in more detail with reference to examples. However, it will be obvious to those skilled in the art that these examples are for illustrative purposes only and are not intended to limit the scope of the present invention.

EXAMPLES

Example 1

Cell Culture 1-1: Cell Culture

Human glioma cell lines (U87MG (ATCC® HTB-14™) and LN18 (ATCC® CRL-2610™)) and the mouse brain endothelial cell line (bEnd3 (ATCC CRL2299™)), purchased from the ATCC, were cultured in DMEM (Dulbecco's modified Eagle's medium) supplemented with 10% FBS (fetal bovine serum) and 100 U/ml penicillin-streptomycin under the conditions of 37° C. and 5% $CO_2$.

1-2: Primary Culture of Neurons and Astrocytes

Cortex was separated from the brains of 1 to 3-day-old mouse (C57BL/6J(B6) male and female mice, Jackson), and then maintained in 0.25% trypsin (Gibco, GIB-25200-072) solution (HBSS solution+6% trypsin+2% L-cysteine) at 37° C. for 20 minutes and separated into individual cells by pipetting. For primary culture, the separated neurons ($7 \times 10^5$ cells/ml) were cultured in Neurobasal-A medium (Gibco, GIB-10888-022) supplemented with 1% L-glutamine, 1% B27 supplement (Gibco, GIB-17504-044) and 100 U/ml penicillin/streptomycin. For primary culture of astrocytes, the separated cells ($4 \times 10^5$ cells/ml) were cultured in DMEM medium supplemented with 10% FBS and 100 U/ml penicillin/streptomycin. When the cells proliferated to form a layer covering the bottom, the cells were treated with 8 μM of Ara-C (arabinofuranosyl cytidine, Sigma C6645) to thereby prevent the proliferation of microglial cells.

Example 2

Western Blotting

Cells (U87MG and LN18) cultured in 6-well plates were incubated in the bidirectional magnetic field application system for 48 hours. Next, the cell lysate was extracted with RIPA buffer (65.21 mM Tris-base, 54 mM NaCl, 1% NP-40, 60.3 mM Na-deoxycholate, and 1 mM EDTA), and the concentration of protein therein was measured using a BCA protein assay kit (Thermo Scientific, 23225). Next, a total of 15 μg of the protein was separated according to size on 10% SDS-PAGE gel, and then electrophoresed for 2 hours and transferred to a PVDF membrane. The PVDF membrane having the protein transferred thereto was blocked with 4% BSA (bovine serum albumin) for 30 minutes, and then incubated in solutions of primary antibodies such as β-catenin (Cell Signaling, 1:2000), phospho-GSK3β (Cell Signaling, 1:1000), caspase-3 (Abcam, 1:200) and β-actin (Santa Cruz Biotech., 1:2000). Subsequently, the membrane was incubated in a solution of HRP-conjugated secondary antibody (Thermo Scientific, 1:5000) for detecting the primary antibodies, and protein band signals were obtained with an ECL kit (Thermo Scientific).

Example 3

Magnetic Field Application System

Figure 1:
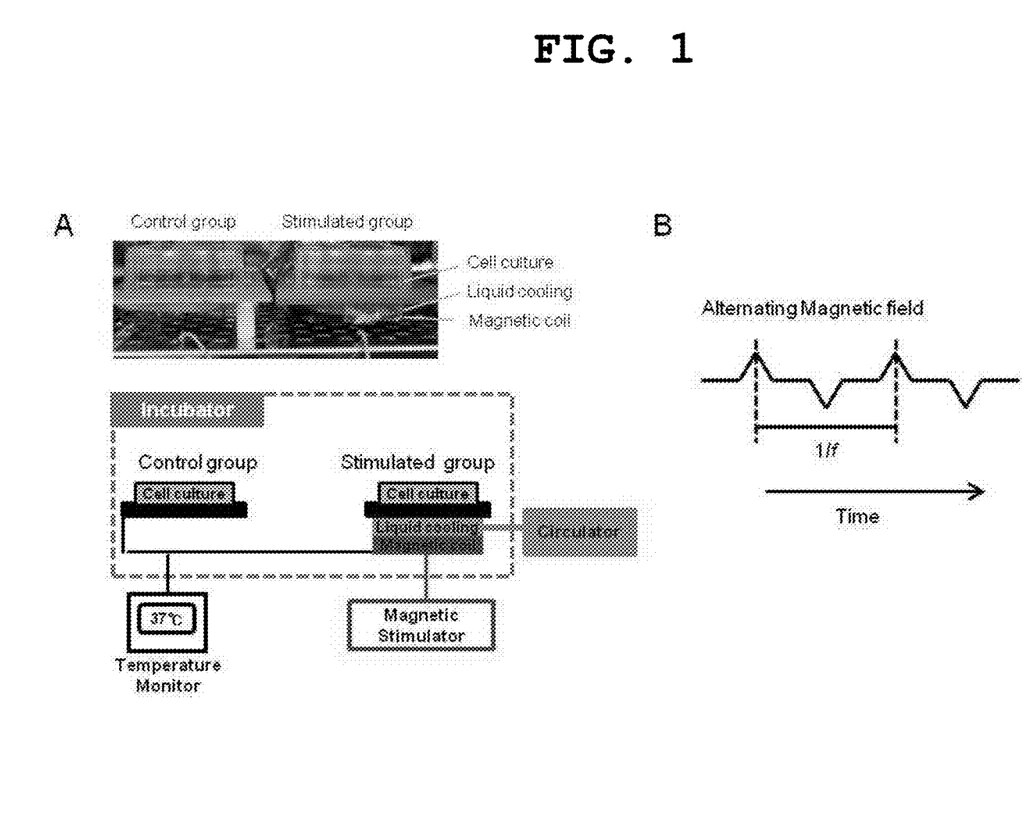
FIG. 1 shows the structure of a bidirectional magnetic field application system according to the present invention.

A bidirectional alternating magnetic field application system was manufactured. The bidirectional alternating magnetic field application system was composed of a coil unit configured to generate a magnetic field, a cooling unit configured to maintain the internal temperature of the system, and an application unit configured to apply the magnetic field, and the application unit configured to apply the magnetic field to cells was manufactured in the form of a plate. The alternating magnetic field application system applicable to animal cells and cultured cells in an incubator at 37° C. was manufactured as shown in FIG. 1A. For a control experiment, a plate was additionally constructed, which did not have a coil and a circulating hose such that magnetic field application would not be applied thereto. A digital control circuit composed of four field effects transistors (FETs) and insulated gate bipolar transistors (IGBTs) produced an alternating magnetic field by the action of a switched-mode power supply (SMPS) that produces a current of up to 40 A. The system was configured such that it would continuously apply a magnetic field having a specific frequency and the magnetic field would have a relatively low frequency (300-500 Hz). A bidirectional magnetic field was generated, and the intensity of the alternating magnetic field produced with repeated waves and different frequencies was maintained constantly at 50-200 Gauss (0.005-0.02 T) (FIG. 1B). The slope of a change in the instantaneous magnetic field intensity of the magnetic field generated from the system was 50 Gauss/100 microsec, which is significantly lower than that in a direct magnetic field or a pulsed magnetic field.

Example 4

Change in Number of Glioma Cells

Figure 2:
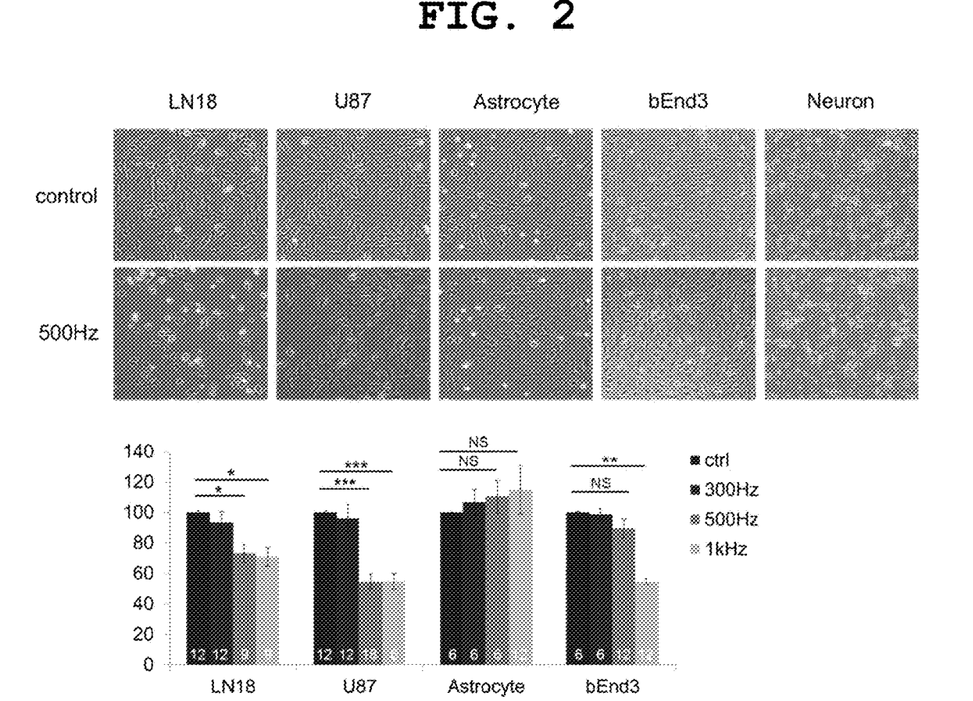
FIG. 2 shows the results of observing changes in the number of malignant glioma cells after applying a magnetic field generated from the bidirectional magnetic field application system of the present invention to these cells.

Cells (LN18, U87MG, endothelial cells (bEND3), astrocytes and neurons) cultured in 96-well plates were placed on a test-group plate to which application from the magnetic field application system was applied and on a control-group plate to which no stimulation was applied. Next, stimulation of a bidirectional alternating magnetic field (0.005 T-0.02 T) with a specific frequency (300-500 Hz) was applied to the test group over 48 hours. The cells were subjected to trypan blue staining, and the number of viable cells in each of the test group and the control group was counted with a hemocytometer. FIG. 2 shows the results of applying the bidirectional alternating magnetic field with 500 Hz and 0.005 T. Meanwhile, no change in the number of non-glioma cells (primary-cultured neurons, astrocytes and endothelial cells) was observed. Application with the magnetic field having a frequency of 1 kHz did not influence neurons and astrocytes, but influenced endothelial cells, and thus it was expected that the use of the magnetic field with a frequency of less than 1 kHz would be safe.

Example 5

Change in Proliferation Rate of Glioma Cells

Figure 3:
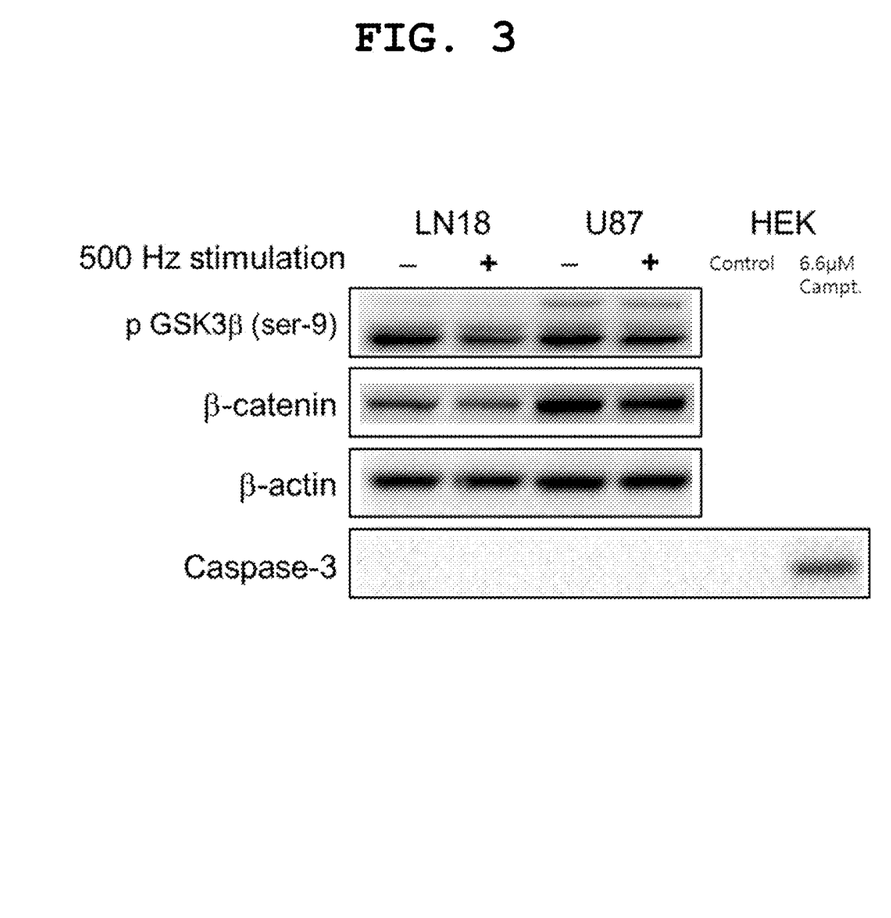
FIG. 3 shows the results of observing the activation of the intracellular Wnt signaling pathway and the induction of apoptosis after applying a magnetic field generated from the bidirectional magnetic field application system of the present invention to cells.

For human glioma cell lines (LN18 and U87MG), a bidirectional alternating magnetic field with a frequency of 300-500 Hz and an intensity of 0.005-0.02 T was applied to the test group over 48 hours, and no magnetic field was applied to the control group. In the test group and the control group, the level of Wnt/β-catenin protein in the cells was lower in the magnetic field stimulation-applied test group than in the control group. FIG. 3 shows the results of applying the bidirectional alternating magnetic field with 500 Hz and 0.005 T. Meanwhile, active caspase-3, which is the representative protein of the apoptotic signaling system, was not substantially detected. Such results support that bidirectional alternating magnetic field application according to the present invention does not induce the apoptosis of glioma cells, but induces a decrease in the proliferation rate of glioma cells.

Example 6

Change in Migration of Glioma Cells

Figure 4:
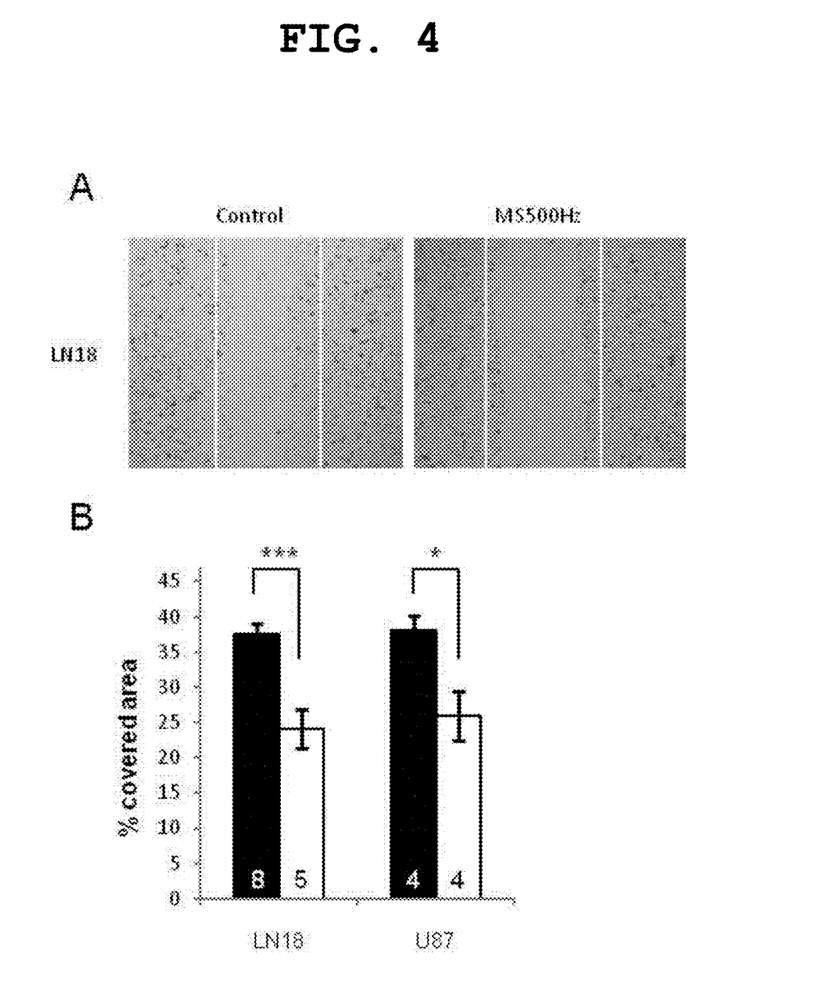
FIG. 4 shows the results of observing whether or not the metastasis of malignant glioma cells was inhibited, after applying a magnetic field generated from the bidirectional magnetic field application system of the present invention to these cells.

Rapid metastasis of glioma cells is associated with the rapid movement and invasion of glioma cells into the surrounding brain tissue. When the cells (U87MG and LN18) cultured in 24-well plates formed a single layer covering the bottom, the cells were scratched with a 10 μl pipette tip to make a space, and then treated with 10 μmol/L of 5'-fluoro-5'-uridine to prevent the proliferation thereof. Next, the cells were incubated in the magnetic field application system of Example 3 for 12 hours. The degree of filling of the scratched space with the cells was analyzed by Image J to determine the mobility of the incubated cells. The migration rate of the LN18 and U87MG cells incubated with magnetic field application significantly decreased (FIG. 4).

Example 7

Change in Calcium in Glioma Cells

Figure 5:
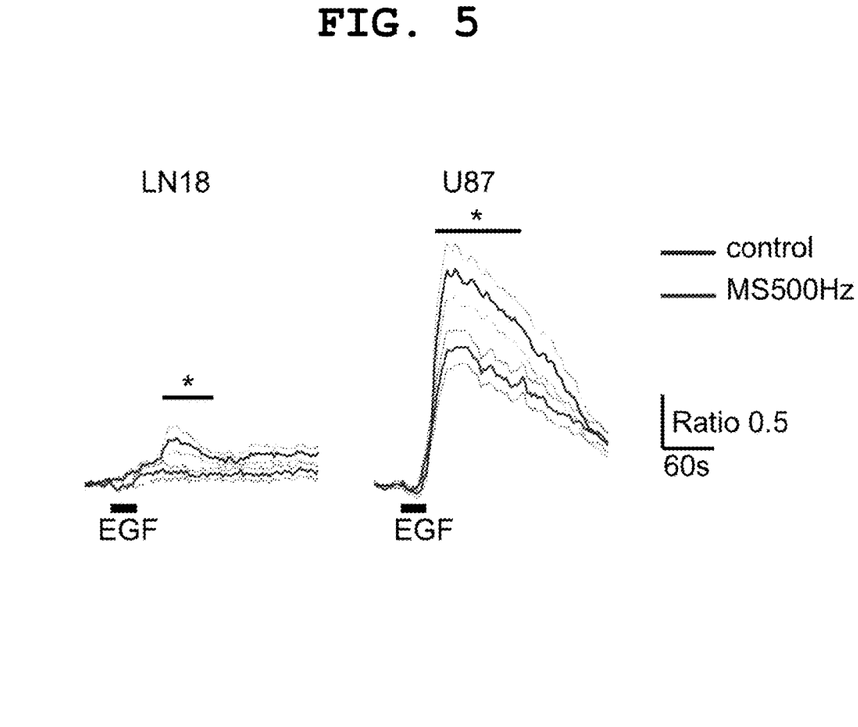
FIG. 5 shows the results of observing calcium movement in malignant glioma cells after applying a magnetic field generated from the bidirectional magnetic field application system of the present invention to these cells.

Cells (LN18 and U87MG) cultured in 24-well plates were incubated in the magnetic field application system for 48 hours, and then treated with 5 μM/L Fluo-4AM (Molecular Probes®, F14201) and 0.02% pluronic acid (Molecular Probes®, P3000MP) at room temperature for 40-45 minutes in order to detect calcium. Using the system of Example 3, a bidirectional alternating magnetic field with a frequency of 500 Hz and an intensity of 0.005 T was applied to the cells, and then the cells were treated with 200 ng/ml of epidermal growth factor (EGF) in order to increase calcium in the cells while the cells were perfused with HEPES buffer (150 mM NaCl, 3 mM KCl, 10 mM HEPES, 2 mM $MgCl_2$, 2 mM $CaCl_2$, 10 mM glucose, pH 7.4). Next, a change in the amount of calcium in the cells was observed with a two-photon laser-scanning microscope (Olympus, Japan). To detect Fluo-4AM fluorescence, a change in the intensity of fluorescence was measured using a bandpass filter (FF01-720/SP-25, FF02-525/40-25; Semrock, USA) and a high-sensitivity GaAsP PMT (H7422-40; Hamamatsu, Japan) at 30 frames/sec, and then a change in relative intensity (ΔF/F) was measured by Image J, thereby determining a change in calcium. Because a change in calcium in cells influences the proliferation and migration pattern of the cells, it was expected that the effect of the bidirectional alternating magnetic field on the proliferation and mobility of cells would be associated with a change in calcium in the cells. It was observed that the change in calcium in the glioma cells to which the magnetic field was applied was significantly lower than that in the control group not treated with the magnetic field (FIG. 5).

As described above, the use of an alternating magnetic field generated from the bidirectional alternating magnetic field application system according to the present invention makes it possible to selectively inhibit the proliferation of malignant glioma cells without causing damage to normal cells, and can inhibit the metastasis of malignant glioma cells into other normal tissues. Thus, according to the present invention, it is possible to prevent the proliferation of malignant glioma cells found before surgery, the rapid metastasis of malignant glioma cells into the surrounding tissues, and the possibility of recurrence caused by malignant glioma cells remaining after surgery. In addition, the method of treating brain tumor by inhibiting malignant glioma cells using a bidirectional alternating magnetic field according to the present invention can greatly reduce side effects occurring in patients after surgery, compared with that of the existing art.

What is claimed is:

1. A bidirectional alternating magnetic field application system, the system comprising:
    a digital control circuit including four field effects transistors (FETs) and insulated gate bipolar transistors (IGBTs) configured to produce a current; and
    a magnetic coil configured to generate a bidirectional alternating magnetic field to be applied to U87MG or LN18 glioma cells,
    wherein a slope of a change in an instantaneous magnetic field intensity of the magnetic field being applied is 50 Gauss/100 microsec or less, the intensity of the magnetic field being applied is 50-200 Gauss, and a frequency of the magnetic field being applied ranges from 300-500 Hz such that the system is configured to inhibit proliferation of the U87MG or LN18 glioma cells and to reduce migration of the U87MG or LN18 glioma cells.

2. A method of preventing or treating a brain tumor in an animal, the method comprising;
    producing a current using a digital control circuit, wherein the digital control circuit includes four field effects transistors (FETs) and insulated gate bipolar transistors (IGBTs);
    generating a bidirectional alternating magnetic field using a magnetic coil; and
    applying the bidirectional alternating magnetic field to U87MG or LN18 glioma cells using the digital control circuit and the magnetic coil,
    wherein a slope of a change in an instantaneous magnetic field intensity of the magnetic field being applied is 50 Gauss/100 microsec or less,
    wherein the intensity of the magnetic field being applied is 50-200 Gauss, and wherein a frequency of the magnetic field being applied ranges from 300-500 Hz.

3. The method of claim 2, wherein the applying of the magnetic field is performed for 24-72 hours.

* * * * *